(12) United States Patent
Forman et al.

(10) Patent No.: US 7,531,578 B2
(45) Date of Patent: May 12, 2009

(54) COMPOUNDS AND METHODS FOR TREATING BREAST CANCER AND OTHER DISEASES

(75) Inventors: Barry Forman, Irvine, CA (US); Donna Yu, Arcadia, CA (US)

(73) Assignee: City of Hope, Duarte, CA (US)

( * ) Notice: Subject to any disclaimer, the term of this patent is extended or adjusted under 35 U.S.C. 154(b) by 580 days.

(21) Appl. No.: 10/944,577

(22) Filed: Sep. 16, 2004

(65) Prior Publication Data

US 2005/0096384 A1    May 5, 2005

Related U.S. Application Data

(60) Provisional application No. 60/504,261, filed on Sep. 18, 2003.

(51) Int. Cl.
*A01N 33/02* (2006.01)
*A01N 43/42* (2006.01)

(52) U.S. Cl. ...................... 514/648; 514/324
(58) Field of Classification Search ................ 514/648, 514/324
See application file for complete search history.

(56) References Cited

U.S. PATENT DOCUMENTS

| 2,502,324 | A | * | 3/1950 | Kaiser et al. ................ | 568/646 |
| 4,623,660 | A | * | 11/1986 | Richardson ................ | 514/514 |

FOREIGN PATENT DOCUMENTS

| CA | 2064509 | * | 10/1993 |
| EP | 0011372 A1 | * | 10/1979 |
| GB | 11372 | * | 5/1980 |

OTHER PUBLICATIONS

Calamita et al. STN Accession No. 1991:551119; Document No. 115:151119; abstract of American Journal of Physiology, 1991, 261 (1, Pt.2), F144-152.*
Vilkas et al. STN Accession No. 1982:405897; Document No. 97:5897; abstract of European Journal of Medicinal Chemistry (1982), 17(2), 191-2.*
Clark et al. STN Accession No. 1966:18865; Document No. 64:18865; abstract of Journal of the Chemical Society (1965), (Nov.), 6509-19.*
Lubczyk et al. Journal of Medicinal Chemistry, 2002, 45, 5358-5364, p. 5359, Table 1.*
Coward, P. et al. "4-Hydroxytamoxifen binds to and deactivates the estrogen-related receptor γ." *Proc. Natl. Acad. Sci. USA* 15:8880-8884 (2001).
Detsi, A. et al. "Synthesis of (Z)-4-Hydroxytamoxifen and (Z)-2-[4-[1-(p-Hydroxyphenyl)-2-phenyl]-1-butenyl] phenoxyacetic Acid." *J. Org. Chem.* 67:4608-4611 (2002).
Dodds, E. C. et al. "Synthetic oestrogenic compounds related to stilbene and diphenylethane. Part I." *Proc. R. Soc. London Ser. B* 127:140-167 (1939).
Gauthier, S. et al. "New Highly Stereoselective Synthesis of (Z)-4-Hydroxytamoxifen and (Z)-4-Hydroxytoremifene via McMurry Reaction." *J. Org. Chem.* 61:3890-3893 (1996).
Giguere, V. "To ERR in the Estrogen Pathway." *Trends in Endocrinology & Metabolism, Review.* 13(5):220-25 (2002).
Giguere, V. et al. "Identification of a new class of steroid hormone receptors." *Nature* 331:91-94 (1988).
Ichida, M. et al. "Identification of a specific molecular repressor of the peroxisome proliferator-activated receptor γ Coactivator-1 α (PGC-1α)." *J. Biol. Chem.* 277(52):50991-95 (2002).
Jarman, M. et al. "The Use of Octafluorotolune and Pentafluoropyridine in the Synthesis of Pure Z- and E-Isomers of Derivatives of Tamoxifen {1,2-Diphenyl-1-[4-(2-dimethylaminoethoy)-phenyl]but-1-ene}." *J. Chem. Research (S)* 116-117 (1985).
Jordan, V. C. "Antiestrogens and selective estrogen receptor modulators as multifunctional medicines. 1. Receptor interactions." *J. Med. Chem.* 46(6):883-908 (2003).
Karnik, P. S. et al. "Estrogen receptor mutations in tamoxifen-resistant breast cancer." *Cancer Res.*, 54:349-353 (1994).
Katzenellenbogen, B. S. et al. "Bioactivities, estrogen receptor interactions, and plasminogen activator-inducing activities of tamoxifen and hydroxy-tamoxifen isomers in MCF-7 human breast cancer cells." *Cancer Res.*, 44:112-119 (1984).
Liu, D. et al. "Estrogen Stimulates Estrogen-Related Receptor α Gene Expression Through Conserved Hormone Response Elements." *Endocrinology*, 144(11):4894-4904 (2003).
Lubczyk, V. et al. "Antiestrogenically active 1,1,2-tris(4-hydroxyphenyl)alkenes without basic side chain: Synthesis and biological activity." *J. Med. Chem.* 46:1484-1491 (2003).
Lubczyk, V. et al. "Investigations on estrogen receptor binding. The estrogenic, antiestrogenic, and cytotoxic properties of C2-alkyl-substituted 1,1-bis(4-hydroxyphenyl)-2-phenylethenes." *J. Med. Chem.*, 45:5358-5364 (2002).
McMurry, J.E. et al. "Improved procedures for the reductive coupling of carbonyls to olefins and for the reduction of diols to olefins." *J. Org. Chem.*, 41:896-97 (1976).
Riggs, B.L. et al. "Selective Estrogen-Receptor Modulators—Mechanisms of Action and Application to Clinical Practice." *N Engl J Med* 384:618-29 (2003).
Robertson, D. W. et al. "Tamoxifen Antiestrogens. A Comparison of the Activity, Pharmacokinetics, and Metabolic Activation of the Cis and Trans Isomers of Tamoxifen." *J. Steroid Biochem.*, 16:1-13 (1982).
Schneider, M. R. "2-Alkyl-substituted 1,1-bis (4-acetoxyphenyl)-2-phenylethenes. Estrogen receptor affinity, estrogenic and antiestrogenic properties, and mammary tumor inhibiting activity." *J. Med. Chem.*, 29(8):1494-1498 (1986).
Schneider, M. R. et al. "1,1,2-Triphenylbut-1-enes: Relationship between structure, estradiol receptor affinity, and mammary tumor inhibiting properties." *J. Med. Chem.*, 25:1070-1077 (1982).
Schreiber, S.N. et al. "The Transcriptional Coactivator PGC-1 Regulates the Expression and Activity of the Orphan Nuclear Receptor Estrogen-Related Receptor α(ERRα)." *J. Biol. Chem.* 278(11):9013-9018 (2003).
Tremblay G.B. et al. "4-Hydroxytamoxifen is an Isoform-Specific Inhibitor of Orphan Estrogen-Receptor-Related (ERR) Nuclear Receptors β and γ." *Endocrinology*, 142(10):4572-75 (2001).

* cited by examiner

*Primary Examiner*—D. Margaret Seaman
*Assistant Examiner*—Nizal S Chandrakumar
(74) *Attorney, Agent, or Firm*—Perkins Coie LLP; Lauren Sliger

(57) ABSTRACT

Disclosed are novel compositions and novel methods for the creation of both the novel compounds and known compounds. Also disclosed are methods for use of the novel compounds for treating a variety of diseases relating to decreasing or preventing activation of estrogen receptors and/or estrogen related receptors.

1 Claim, No Drawings

COMPOUNDS AND METHODS FOR TREATING BREAST CANCER AND OTHER DISEASES

PRIORITY CLAIM

This application claims priority to U.S. Provisional Application Ser. No. 60/504,261, filed Sep. 18, 2003, which is incorporated herein by reference.

FIELD OF THE INVENTION

This invention relates to novel chemical compounds that modulate the activity of estrogen receptors (ERα,β) and estrogen-related receptors (ERRα,β,γ), novel methods of synthesizing the novel compounds and other compounds, and methods for use of both the products and methods.

BACKGROUND OF THE INVENTION

Each of the references cited herein is incorporated by reference in its entirety. A complete listing of the citations is set forth at the end of the specification.

An estimated 211,300 new cases of invasive breast cancer are expected to occur among women in the United States during 2003. Breast cancer is the most frequently diagnosed non-skin cancer in women. (1) Estrogen is a steroid hormone that, while having important functions including the control of reproduction and the development of secondary sexual characteristics, also plays a predominant role in breast cancer growth and development. The use of estrogen for its positive effects can also detrimentally result in the stimulation of other tissues, such as those of the breast and uterus, and increase the risk of cancer at these sites.

The estrogen receptor (ER) is a member of a nuclear receptor superfamily consisting of orphan receptors and receptors for classic high-affinity ligands, such as steroid hormones, vitamin D, retinoids, and thyroid hormones. As a ligand inducible transcription factor, the estrogen receptor mediates the activity of estrogen in the development and function of the female reproductive system, the maintenance of bone mineral density, regulation of blood lipid profile, brain function, cardiovascular health and other physiologic processes.

Estrogen-Related Receptors (ERRs) are included in the nuclear receptor family and were the first orphan nuclear receptors found through a search for genes encoding proteins related to known nuclear receptors. While it was originally believed that the development and physiological roles of ERRs were quite distant from those of the classic ERs, it has recently been shown that in some cases ERRs can share target genes, coregulatory proteins, ligands, and sites of action with the ERs. (2) Like ER, ERRs are also implicated in breast cancer and other diseases. (3)

(Z)-Tamoxifen (Z-TAM), (Z)-2-[4-(1,2-diphenyl-1-butenyl) phenoxy]N,N-dimethylethanamine, is used clinically to treat estrogen-dependent breast cancer by acting as an antagonist of estrogen-induced tumor growth. The mechanism for its principal action is its competition with the natural agonist hormone estradiol ($E_2$) for binding to the estrogen receptor ligand-binding domain, thereby reducing the ability of estradiol to stimulate nuclear transcription and consequent cell growth. For example, it is known that (Z)-4-hydroxytamoxifen (4-OHT), a potent tamoxifen metabolite, is a selective estrogen-receptor modulator that functions as an antagonist in breast cancer cells but displays estrogen-like activities in the uterus and bone. The Z-4-OHT form isomer has the required antiestrogenic activity, but E-4-OHT isomer has only about 5% of its affinity for ER. (17)

Selective Estrogen-Receptor Modulators (SERMs) are a type of estrogen receptor ligand that can exert agonist, antagonist, or neutral effects, depending on factors including the target gene and/or target tissue. (2) SERMs properties are related to their ability to compete in target tissues with estradiol for binding sites in the ligand-binding domain (LBD) of the ER. Tamoxifen and particularly its metabolite 4-hydroxytamoxifen are SERMs that also antagonize ERRs, but much higher doses of those SERMs are required to antagonize ERRs than ERs. In recent studies examining whether other ER ligands could influence ERR activity, (Z)-4-OHT was identified as the most potent isoform-specific inhibitor of ERRβ,γ. (4) The structures of (Z)-TAM, (Z)-4-OHT, and $E_2$ are:

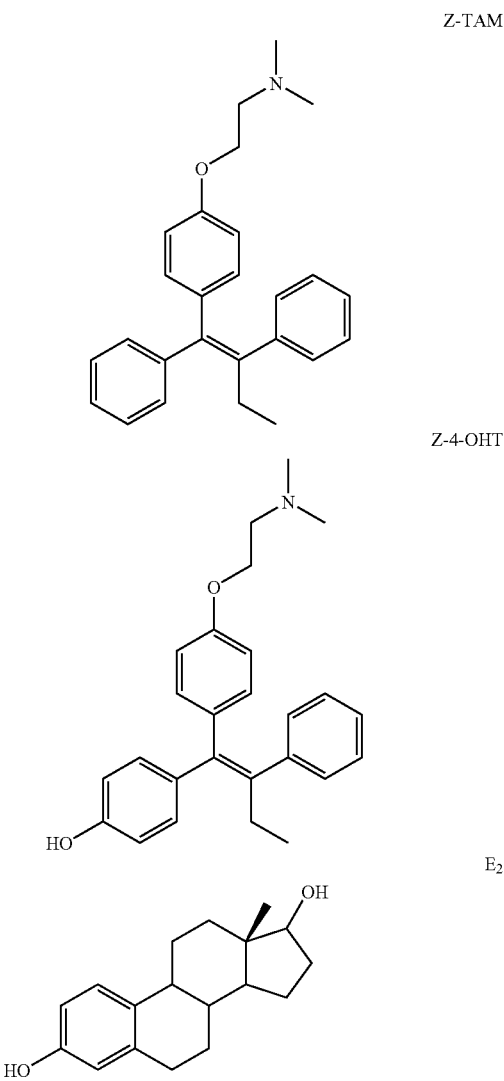

Recent experiments have synthesized 1,1-bis and 1,1,2-tris (4-hydroxyphenyl)-2-phenylalkene analogs for the studies of their antagonist action. (5) Studies also have shown that 1,1, 2-triarylethenes are antagonists and that they inhibit the effect of 1 nM $E_2$, dependent on the length of C2-alkyl chain. When C2 is substituted by an ethyl or trifluoromethyl group of the 1,1,2-triarylethene system, the substituted compound possesses the same antagonistic potency as 4-hydroxytamoxifen and is almost 50 times more active than tamoxifen itself. (6)

None of the 1,1-bis- and 1,1,2-tri (4-hydroxyphenyl)-2-phenylalkylenes bear a basic side chain, which is responsible for antagonistic effects of ER. Removal of the dimethylaminoethoxy side chain of 4-hydroxytamoxifen did not decrease the antagonistic effects on the MCF-7-2a cell line. This finding indicated that, in the class of 1,1-bis- and 1,1,2-tris (4-hydroxyphenyl)-2-phenylalkenes, having a basic side chain is not a prerequisite for exhibiting high binding affinity and antagonistic effects on ER. The antiestrogenic properties comprising estrogen receptor binding depend only on the length of the C2-alkyl chain.

Other experiments have also revealed information about the various ERRs. Estrogen Related Receptor Alpha ("ERRα" or "ERRa") binds the ligand diethylstilbestrol (DES) with greater affinity than 4-hydroxytamoxifen as antagonist/inverse agonist. ERRα functions to control adiposity and energy metabolism. In experiments with ERRα knockout mice, the mice are lean. ERRα also regulates the medium-chain acyl-CoA dehydrogenase (MCAD) gene in conjunction with PGC-1α (peroxisome proliferator-activated receptor gamma coactivator 1), a key regulator of lipid and glucose homeostasis.

PGC-1α is a transcriptional co-activator that regulates numerous pathways controlling both metabolism and overall energy homeostasis. (15) ERRα binding to PGC-1α requires the AF2 domain of ERRα. PGC-1α induces the expression of ERRα, meaning that ERRα is upregulated in response to signals that induce PGC-1α, such as exposure to cold. Expression of PGC-1α led to the induction of ERRα at the RNA and protein level in SAOS2-GR(+) cells, as well as in HtTA-1, HepG2, and 293 cells.

It has been found that PGC-1α and ERRα have a similar pattern of expression in human tissues, with both being present predominantly in organs with high metabolic needs such as skeletal muscle, kidney, and heart. Physiological stimuli such as fasting coordinately induces PGC-1α and ERRα. ERRα can dramatically and specifically repress PGC-1α transcriptional activity. (7)

ERRα is known to be expressed in breast cancer cells and it inhibits breast cancer cell growth independent of the estrogen receptor. ERRα regulates aromatase and pS2 genes and is associated with unfavorable biomarkers in human breast cancer. ERRα is also expressed in osteoblasts and regulates osteopontin expression. A recent study demonstrates that the ERRα gene is a downstream target of ERα. (16)

Estrogen Related Receptor Beta ("ERRβ" or "ERRb") binds the ligand 4-hydroxytamoxifen with a greater affinity than DES as antagonist/inverse agonist. ERRβ controls trophoblast proliferation and placental, function. In mice lacking ERRβ, trophoblast stem cell differentiation is impaired and the placenta fails to develop normally. (8) ERRβ is present early in the developing placenta in a subset of cells in extra-embryonic ectoderm destined to make up the chorion. (8,9) Thus, ERRβ is likely essential for reproduction. ERRβ synthesis is highly restricted in postnatal life, being detected at low levels in the liver, stomach, skeletal muscle, heart and kidney. (5)

Estrogen Related Receptor Gamma ("ERRγ" or "ERRg") binds the ligand 4-hydroxytamoxifen with a greater affinity than DES as antagonist/inverse agonist. ERRγ is expressed in heart, skeletal muscle, kidney, and brain as well as in the developing nervous system. Human ERRγ transcripts can be detected at very high levels in fetal brain, and at lower levels in fetal kidney, lung and liver. (4) In adult tissues, ERRγ is widely expressed and can be detected in brain, lung, bone marrow, adrenal and thyroid glands, trachea and spinal cord. In the mouse, the gene encoding ERRγ is expressed in specific areas of the brain, in addition to the heart, kidney, muscle, spleen and testis. With respect to its role in breast cancer, ERRγ associates with favorable biomarkers in human breast cancer and may regulate MCAD.

ERRα, ERRβ, and ERRγ do not respond to natural estrogens. They do recognize, however, the estrogen response element and can modulate gene expression in the absence of exogenously added ligand. 4-OHT disrupts the interaction between ERRβ and its co-regulator proteins and ERRγ and its co-regulator proteins. 4-OHT also abolishes the constitutive transcriptional activity of these receptors in transient transfection assays. In contrast, 4-OHT has no effect on coregulator/ERRα interaction or its transcriptional activity, demonstrating the existence of a novel nuclear receptor-based pharmacological pathway that may contribute to the tissue-specific activities of 4-OHT. (10)

Thus, ERs and ERRs are clearly targets of modulation, particularly of antiproliferative therapy. There is a pressing need, however, for compounds that modulate these receptors more effectively. There is also a need for methods of using these compounds to treat estrogen-related disorders, particularly breast cancer. Further, there is always a need for an inexpensive and efficient method to synthesize compounds for use as pharmaceuticals, and here, particularly for compounds used to treat breast cancer.

SUMMARY OF THE INVENTION

The first aspect of the present invention is the creation of a number of novel compounds that modulate estrogen receptors (ERs) and estrogen-related receptors (ERRs). Preferably, modulation of the ERs and ERRs occurs through the action of novel compounds antagonizing the receptors. These compounds are highly effective, with some of the most preferred compounds being thirty times more effective at antagonizing ERRβ and ERRγ than 4-hydroxytamoxifen. It is preferred that the novel compounds modulate both ERs and ERRs simultaneously. It is further favorable if the modulation occurs through antagonization of ERs and ERRs. Preferably, the novel compounds (or pharmaceutically acceptable salt or pro-drug there of) have the structure of:

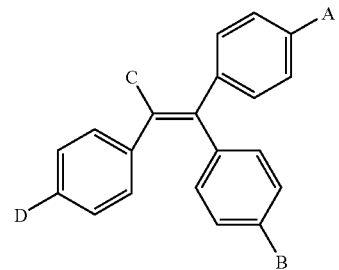

wherein A is —OCH$_2$(CH$_2$)$_{10}$CH$_3$, —OH, —OCH$_2$CHCH$_2$, optionally-substituted alkyl and alkenyl ethers, or

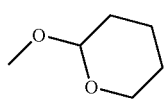 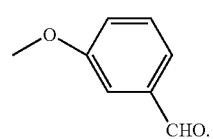

B is optionally —CHC(CH$_3$)$_2$, —CH(CH$_3$)$_2$, —C(CH$_3$)$_3$, —CH$_2$CHCH$_2$, or optionally-substituted alkyl, alkenyl and alkynyl groups;

C is —OH, —OCH$_2$(CH$_2$)$_{10}$CH$_3$, —OCH$_2$CHCH$_2$, optionally-substituted alkyl and alkenyl ethers, or

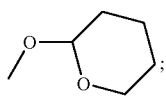

and

D is optionally —CH$_2$CHCH$_2$, or substituted alkyl, alkenyl and alkynyl groups. Optional substituents may also include halogen atoms, haloalkyl and optionally-substituted alkylcarboxy, alkoxy, phenoxy, alkylamino and alkylcarbonyl groups. These compounds are designated as a class called Novel Compounds 1.

The novel compounds (or pharmaceutically acceptable salt or pro-drugs thereof) of the present invention may also have the structure of:

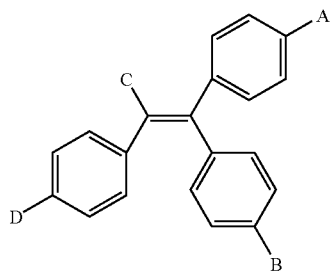

wherein A is —OH,

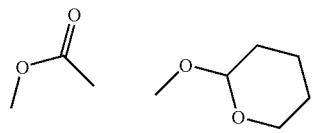

or optionally-substituted alkyl, alkenyl esters and ethers;

B is —OH, —O(CH$_2$)$_n$NR$_1$R$_2$ where R$_1$ and R$_2$ represent a hydrogen atom, or optionally-substituted alkyl, alkenyl, alkynyl or phenyl groups. Most preferably, R$_1$ is —CH$_3$ and R$_2$ is a —CH$_3$ group. Preferred optional substituents include halogen atoms, haloalkyl, and alkylcarboxy, alkoxy, phenoxy, alkylamino and alkylcarbonyl groups. B may also be

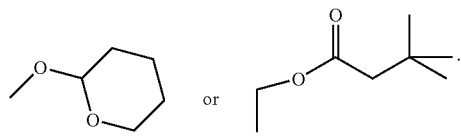

C is optionally —CH$_2$CH$_3$, —CH(CH$_3$)$_2$, —CH$_2$CH(CH$_3$)$_2$, —CH$_2$Cl, —CH$_2$CH$_2$Cl, —CH$_2$CH$_2$CH$_2$Cl, or optionally-substituted alkyl, alkenyl, alkynyl groups; and D is optionally —H, —OH, —CH$_3$, or halogen atoms. This novel compound does not comprise the structure of DY25, DY27 or DY33. These compounds are designated as a class called Novel Compounds 2. Both Novel Compounds 1 and 2 may exist in different isomeric forms and the formulas are not intended unless otherwise stated herein, to be limited to any such form.

If the compounds are a member of Novel Compounds 1, preferably, they comprise the structure of DY14, DY15, DY16, DY17, DY18, DY19, DY20, DY21, DY22, DY23, or DY24. If the compounds are a member of Novel Compounds 2, preferably, they comprise the structure of DY26, DY28, DY29, DY30, DY31, DY34, DY35, DY39, or DY40. Most preferably, the novel compound comprises the structure of DY40.

A second aspect of the present invention is a novel synthesis method that enables the creation of the novel compounds described herein, other novel compounds, and also provides a superior method for making known compounds. The compounds created by the novel method may be of many kinds depending on the precursors used, but are generally substituted triphenylethylene derivatives (General Formula I) with a structure of:

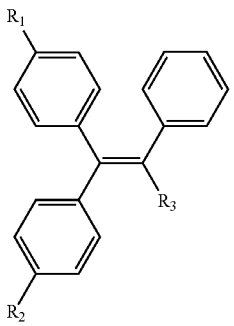

It is preferred that the compounds are substituted-triarylethylenes. R$_1$, R$_2$, and R$_3$ each independently represent an optional alkyl, alkenyl, or alkynyl group. Other optional substituents include halogen atoms, haloalkyl and hydroxy groups and substituted alkylcarboxy, alkoxy, alkylamino and alkylcarbonyl groups. The compound of General Formula I may exist in different geometric isomeric forms and the formula depicted above is not intended as a limitation.

An aspect of this synthesis portion of the invention uses a novel McMurry coupling reaction of 1,1-bis (4-hydroxyphenyl)-2-phenylalkene analogs as precursors with which to ultimately construct DY40, with DY27 (4-hydroxytamoxifen) as an intermediate product. The novel method of making the novel compounds bypasses a cumbersome five-step procedure currently used in the art.

A third aspect of the present invention is a method of treating diseases or disorders relating to the ERs and/or ERRs. Preferably, the disease is a proliferative disease, obesity, stroke, hormonal disorders, lipidemia and other lipid disorders, metabolic disorders, Syndrome X, diabetes, diseases related to fetal development, osteoporosis or heart disease. If the disease is a proliferative disease, preferably, the disease to be treated is cancer. Most preferably, the proliferative disease treated by the methods of the present invention is breast cancer. The method comprises administering at least one of the novel compounds to a subject in need thereof in a pharmaceutically acceptable carrier and in a pharmaceutically effective amount. Preferably, the administration is repeated to maintain a therapeutically effective amount of the at least one novel compound in the blood stream and/or at the location of the cancer over time until treatment is effected.

In a preferred embodiment, the estrogen-related disease is treated in the subject as a result of one or more novel compounds being administered to a subject and modulating an estrogen receptor, an estrogen related receptor, or modulating both estrogen receptors and estrogen related receptors. Preferably, the modulation is an antagonizing action, although it may also neutralize or agonize the receptors. More preferably, the receptors modulated are ERRβ or ERRγ. It is also preferred that antagonizing an estrogen receptor occurs by preventing an agonist from binding to the ligand binding domain of the receptor. For an estrogen related receptor, which is constitutively active, it is preferred that the mechanism is antagonism occurs by the novel compound binding directly to the ligand binding domain of the receptor.

In another preferred aspect, the novel compound administered to a subject in need thereof is DY40, which may be administered alone or in combination with other novel compounds or known treatments for a given disease or disorder. While the DY40 and/or other novel compounds can be administered directly to the subject, it is preferable that they are administered in a pharmaceutically effective carrier. The DY40 is either administered into a system that will bring the DY40 in contact with the affected area, or is contacted directly with the affected cells, tissues, or organs. It is possible that the treatment comprises a combination of these two methods. In addition, it is preferred that DY40 is administered in a pharmaceutically effective amount. The administration of the at least one novel compound is preferably by the oral, intravenous, parenteral, nasal, or transdermal route. The combined dosage of the at least one novel compound is preferably between 1 mg/day and 1 g/day, more preferably between 20 mg/kg and 750 mg/kg per day, and most preferably between 50 mg/day and 500 mg/day.

In the most preferred aspect of the invention, DY40 antagonizes ERRβ and ERRγ, which treats breast cancer in a subject. DY40 is administered to the subject in a pharmaceutically effective amount and in a pharmaceutically acceptable carrier. The preferred dosage of DY40 is in an amount of between 1 mg/day and 1 g/day, more preferably between 20 mg/kg and 750 mg/kg per day, and most preferably between 50 mg/day and 500 mg/day.

These and other preferred aspects of the present invention are elucidated further in the detailed description.

DETAILED DESCRIPTION

Definitions

The present invention can best be understood in light of the following definitions.

Generally, an "antagonist" is a ligand that interacts with or binds to its receptor or ligand binding domain to downregulate, suppress, or inhibit the activity of an agonist compound. In the present invention, an ER or ERR antagonist means a molecule or a compound that inhibits or decreases the transcriptional activity of ER or ERR, respectively.

The term "pharmaceutically effective dose" as used herein refers to the amount of either a novel compound or novel compound composition comprising one or more of the novel compounds described herein that produces a desired therapeutic effect, such as treating the target disease. The precise amount of the pharmaceutically effective dose of a novel compound or novel compound composition that will yield the most effective results in terms of efficacy of treatment in a given subject will depend upon the activity, pharmacokinetics, pharmacodynamics, and bioavailability of a particular ERR antagonist, physiological condition of the subject (including age, sex, disease type and stage, general physical condition, responsiveness to a given dosage and type of medication), the nature of pharmaceutically acceptable carrier in a formulation, and a route of administration, among other potential factors. Those skilled in the clinical and pharmacological arts will be able to determine these factors through routine experimentation consisting of monitoring the subject and adjusting the dosage. Remington: The Science and Practice of Pharmacy (Gennaro ed. 20$^{th}$ edition, Williams & Wilkins PA, USA) (2000).

As used herein, the "target disease" may be any disease in which modulating one or more of the ERs, ERRs or a combination of modulating both ERs and ERRs treats the disease. Without limitation, a list of target diseases includes cancer and other proliferative disease, obesity, stroke, hormonal disorders, lipidemia and other lipid disorders, metabolic disorders, Syndrome X, diabetes, diseases related to fetal development, osteoporosis or heart disease. While it is possible for a novel compound to be administered as a pure or substantially pure compound, it is preferable that the ER or ERR be administered as a composition in the form of pharmaceutical formulations or preparations suitable for a particular administration route. A novel compound composition comprises one or more ER and/or ERR modulators and a pharmaceutically acceptable carrier.

The term "pharmaceutically acceptable carrier" as used herein means a pharmaceutically-acceptable material, composition or vehicle, such as a liquid or solid filler, diluent, excipient, solvent or encapsulating material, involved in carrying or transporting one or more ER or ERR modulators from one tissue, organ, or portion of the body, to another tissue, organ, or portion of the body. Each component must be "pharmaceutically acceptable" in the sense of being compatible with the other ingredients of the formulation. It must also be suitable for use in contact with the tissue or organ of humans and animals without excessive toxicity, irritation, allergic response, immunogenecity, or other problems or complications, commensurate with a reasonable benefit/risk ratio. The novel compounds may also be encapsulated with liposomes.

A "route of administration" for a novel compound or composition can be by any pathway known in the art, including without limitation, oral, enteral, nasal, topical, rectal, vaginal, aerosol, transmucosal, transdermal, ophthalmic, pulmonary, and/or parenteral administration. A parenteral administration refers to an administration route that typically relates to injection. Parenteral administration includes, but is not limited to, intravenous, intramuscular, intraarterial, intraathecal, intracapsular, infraorbital, intracardiac, intradermal, intraperitoneal, transtracheal, subcutaneous, subcuticular, intraarticular, subcapsular, subarachnoid, intraspinal, via intrasternal injection, and/or via infusion.

"Treatment" of or "treating" a disease may mean preventing the disease by causing clinical symptoms not to develop, inhibiting the disease by stopping or reducing the symptoms, the development of the disease, and/or slowing the rate of development of the disease, relieving the disease by causing a complete or partial regression of the disease, reducing the risk of developing the disease, or a combination thereof.

The term "contacted" when applied to a cell, tissue or organ means the process by which a novel compound or compound composition is delivered to the target cell, tissue or organ, or placed in direct proximity of the cell, tissue, or organ.

"Therapeutically effective amount" is the amount of novel compound or composition that, when administered to a subject, is effective to bring about a desired effect. In this case, that effect is typically an antagonistic effect that ultimately decreases the activity of the ERs and/or ERRs. The preferred therapeutically effective amount is in an amount of between 1 mg/day and 1 g/day, more preferably between 20 mg/kg and 750 mg/kg per day, and most preferably between 50 mg/day and 500 mg/day.

"Radiotherapeutic agents" or "chemotherapeutic agents" mean any chemical compound or treatment method that induces cell damage and/or results in cell death. Such agents include azathioprine, BCG, androgens, asparagine, bleomycin, epirubicin, gemcitabine, hydroxyurea, interferon alpha, beta or gamma, 6-mercaptopurine, paclitaxel, thioguanine, adriamycin, 5-fluorouracil, etopside, camptothecin, actinomycin-D, mitomycin C, cisplatin, or other drugs. The agents may also include radiation and waves like gamma radiation, X-rays, UV-irradiation, microwaves, and electroemissions. Other chemotherapeutic substances may include natural or synthetic antibodies, metastases-inhibiting compounds, growth factor inhibitors, oncogenic protein inhibitors, such as for inhibiting RAS, protein kinase inhibitors, or DNA topoisomerase inhibitors. These agents may be used in conjunction with the novel DY compounds as an initial treatment or as part of a second-line therapy for tamoxifen-resistant breast cancer. The invention contemplates the use of any of these, alone or in combination, with the novel DY compounds and methods of their use.

"Pro-drug" means any compound that releases a biologically active compound of one of the novel DY formulas in vivo when administered to a subject because there are in vivo modifications of the functional groups that yield the desired DY compound.

Novel DY Compounds

The novel DY compounds (or pharmaceutically acceptable salt or pro-drug there of) of the present invention may be any combination of the following:

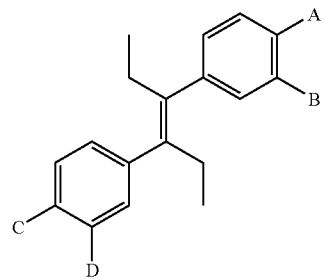

wherein A is —OCH$_2$(CH$_2$)$_{10}$CH$_3$, —OH, —OCH$_2$CHCH$_2$, optionally-substituted alkyl and alkenyl ethers,

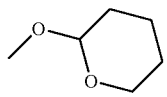 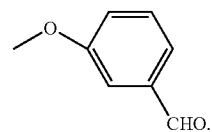

B is optionally —CHC(CH$_3$)$_2$, —CH(CH$_3$)$_2$, —C(CH$_3$)$_3$, or —CH$_2$CHCH$_2$, or optionally-substituted alkyl, alkenyl and alkynyl groups.

C is —OH, —OCH$_2$(CH$_2$)$_{10}$CH$_3$, —OCH$_2$CHCH$_2$, or optionally-substituted alkyl and alkenyl ethers, or

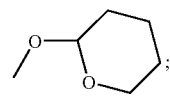

And D is optionally —CH$_2$CHCH$_2$, substituted alkyl, alkenyl and alkynyl groups. Optional substituents may also include halogen atoms, haloalkyl and optionally-substituted alkylcarboxy, alkoxy, phenoxy, alkylamino and alkylcarbonyl groups. Any of these compounds are designated in the group of Novel Compounds 1.

Alternatively, the novel compounds may comprise:

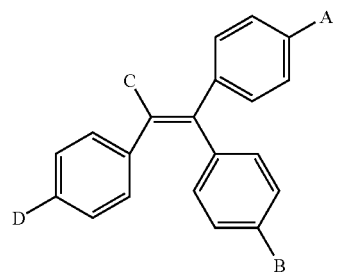

wherein A is —OH, or optionally-substituted alkyl, alkenyl esters and ethers

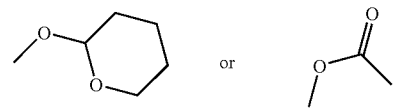

B is —OH, —O(CH$_2$)$_n$NR$_1$R$_2$, wherein R$_1$ and R$_2$ independently represent an optionally-substituted alkyl group, most preferably methyl group,

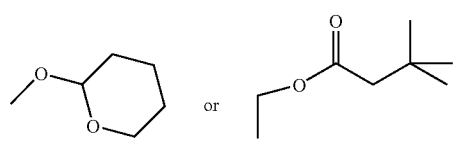

C is optionally —CH$_2$CH$_3$, —CH(CH$_3$)$_2$, —CH$_2$CH(CH$_3$)$_2$, —CH$_2$Cl, —CH$_2$CH$_2$Cl, —CH$_2$CH$_2$CH$_2$Cl, or optionally-substituted alkyl, alkenyl, alkynyl groups. Finally, D is optionally —H, or —OH, —CH$_3$, or halogen atoms. These compounds are designated as a class called Novel Compounds 2. Both Novel Compounds 1 and 2 may exist in different isomeric forms and their formulas are not intended, unless otherwise stated herein, to be limited to any such form.

If the compounds are a member of Novel Compounds 1, preferably, they comprise the structure of DY14, DY15, DY16, DY17, DY18, DY19, DY20, DY21, DY22, DY23, or DY24. The structure, formula, and molecular weight of these compounds are:

-continued

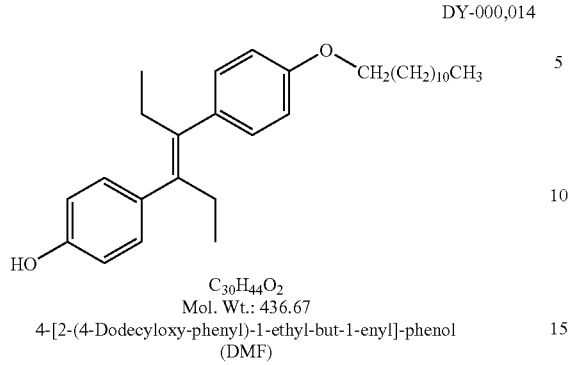

DY-000,014

$C_{30}H_{44}O_2$
Mol. Wt.: 436.67
4-[2-(4-Dodecyloxy-phenyl)-1-ethyl-but-1-enyl]-phenol
(DMF)

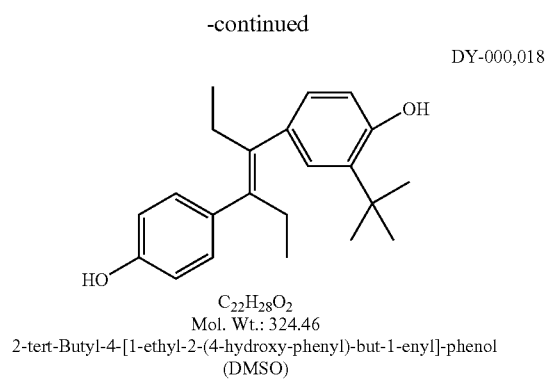

DY-000,018

$C_{22}H_{28}O_2$
Mol. Wt.: 324.46
2-tert-Butyl-4-[1-ethyl-2-(4-hydroxy-phenyl)-but-1-enyl]-phenol
(DMSO)

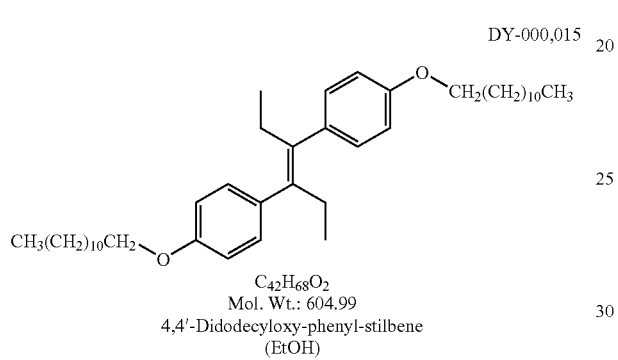

DY-000,015

$C_{42}H_{68}O_2$
Mol. Wt.: 604.99
4,4'-Didodecyloxy-phenyl-stilbene
(EtOH)

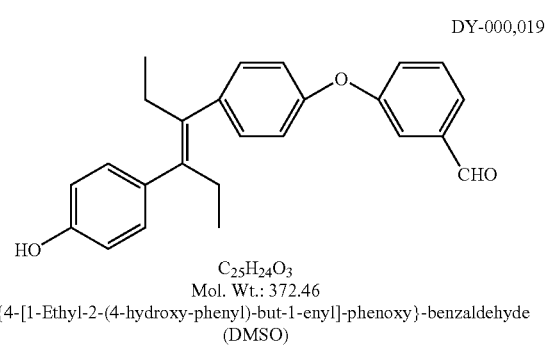

DY-000,019

$C_{25}H_{24}O_3$
Mol. Wt.: 372.46
3-{4-[1-Ethyl-2-(4-hydroxy-phenyl)-but-1-enyl]-phenoxy}-benzaldehyde
(DMSO)

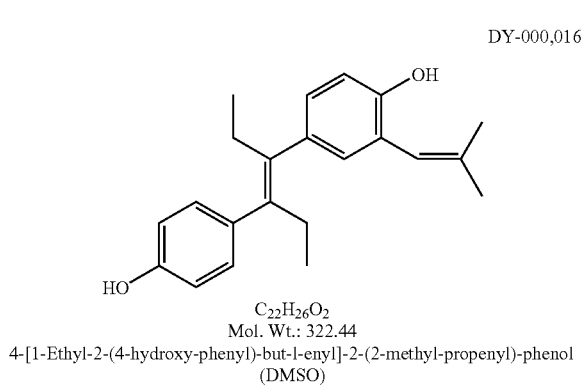

DY-000,016

$C_{22}H_{26}O_2$
Mol. Wt.: 322.44
4-[1-Ethyl-2-(4-hydroxy-phenyl)-but-1-enyl]-2-(2-methyl-propenyl)-phenol
(DMSO)

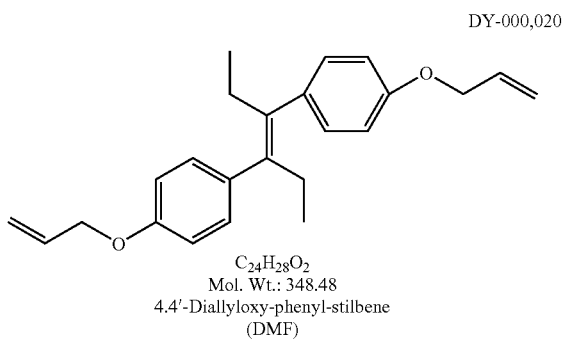

DY-000,020

$C_{24}H_{28}O_2$
Mol. Wt.: 348.48
4,4'-Diallyloxy-phenyl-stilbene
(DMF)

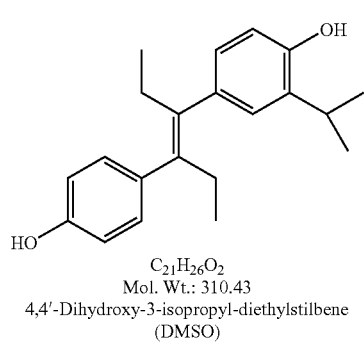

DY-000,017

$C_{21}H_{26}O_2$
Mol. Wt.: 310.43
4,4'-Dihydroxy-3-isopropyl-diethylstilbene
(DMSO)

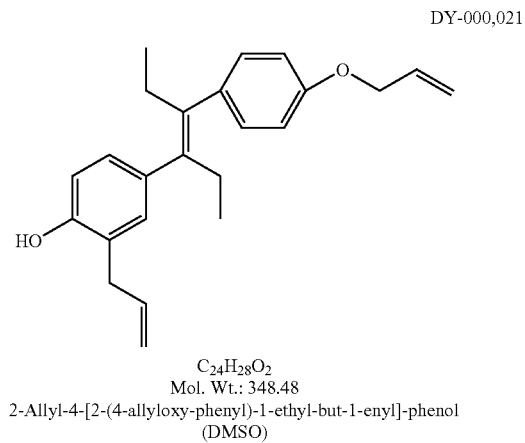

DY-000,021

$C_{24}H_{28}O_2$
Mol. Wt.: 348.48
2-Allyl-4-[2-(4-allyloxy-phenyl)-1-ethyl-but-1-enyl]-phenol
(DMSO)

-continued

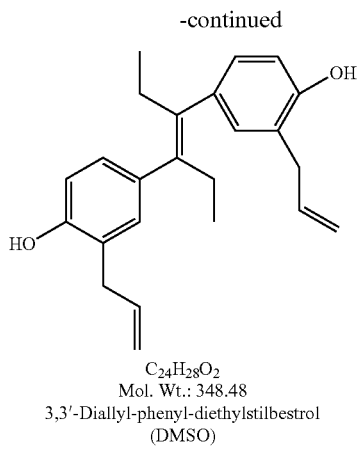

DY-000,022

C$_{24}$H$_{28}$O$_2$
Mol. Wt.: 348.48
3,3'-Diallyl-phenyl-diethylstilbestrol
(DMSO)

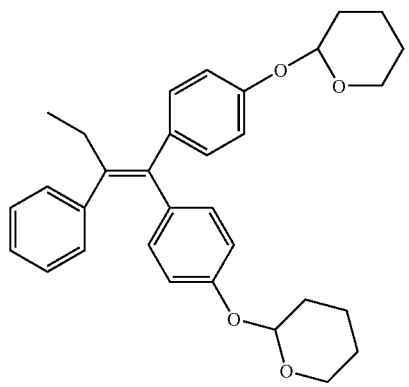

DY-000,026

C$_{32}$H$_{36}$O$_4$
Mol. Wt.: 484.63
4,4'-Ditetrahydropyran-(2-yloxy)-2-phenlbut-1-ene
(DMF)

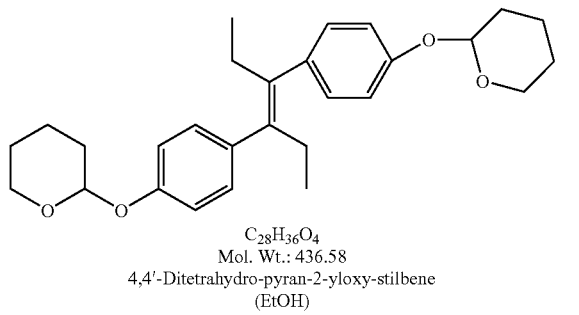

DY-000,023

C$_{28}$H$_{36}$O$_4$
Mol. Wt.: 436.58
4,4'-Ditetrahydro-pyran-2-yloxy-stilbene
(EtOH)

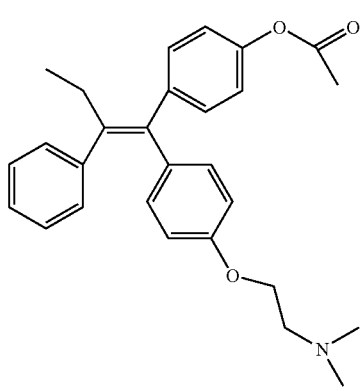

DY-000,028

C$_{28}$H$_{31}$NO$_3$
Mol. Wt.: 429.55
+Z isomer
(E)-Acetic acid 4-{1-[4-(2-dimethylamino-ethoxy)-phenyl]-2-phenyl-but-1-enyl}-phenyl ester
(DMSO)

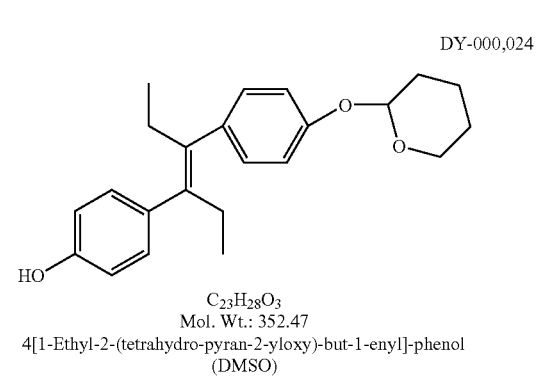

DY-000,024

C$_{23}$H$_{28}$O$_3$
Mol. Wt.: 352.47
4[1-Ethyl-2-(tetrahydro-pyran-2-yloxy)-but-1-enyl]-phenol
(DMSO)

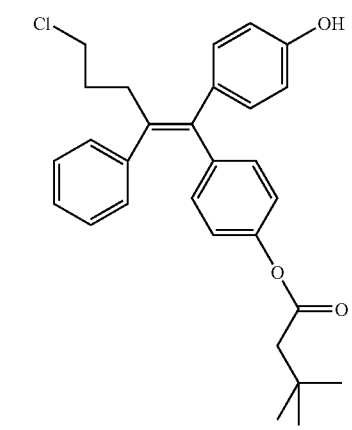

DY-000,029

C$_{29}$H$_{31}$ClO$_3$
Mol. Wt.: 463.01
+E isomer
(Z)-3,3-Dimethyl-butyric acid 4-[5-chloro-1-(4-hydroxy-phenyl)-2-phenyl-pent-1-enyl]-phenyl ester
(DMSO)

If the compounds are a member of Novel Compounds 2, preferably, they comprise the structure of DY26, DY28, DY29, DY30, DY31, DY34, DY35, DY39, or DY40. Most preferably, the novel compound comprises the structure of DY40. The structure, formula, and molecular weight of these compounds are:

-continued

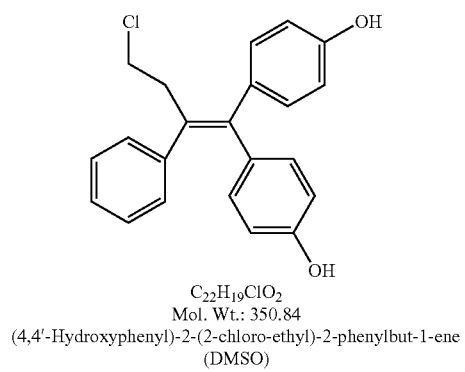

DY-000,030

C₂₂H₁₉ClO₂
Mol. Wt.: 350.84
(4,4'-Hydroxyphenyl)-2-(2-chloro-ethyl)-2-phenylbut-1-ene
(DMSO)

DY-000,031

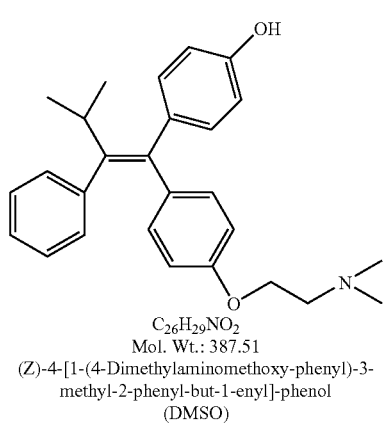

C₂₃H₂₁ClO₂
Mol. Wt.: 364.86
(4,4'-Hydroxyphenyl)-2-(3-chloro-propyl)-2-phenylbut-1-ene
(DMSO)

DY-000,034

C₂₃H₂₂O₂
Mol. Wt.: 330.42
(4,4'-Hydroxyphenyl)-2-isopropyl-2-phenylbut-1-ene
(DMSO)

-continued

DY-000,035

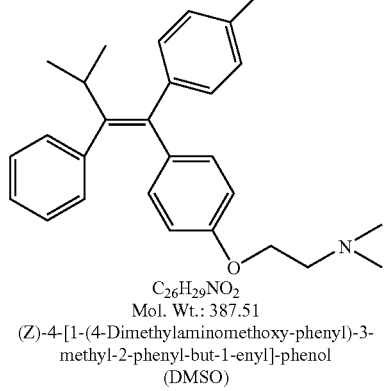

C₂₆H₂₉NO₂
Mol. Wt.: 387.51
(Z)-4-[1-(4-Dimethylaminomethoxy-phenyl)-3-methyl-2-phenyl-but-1-enyl]-phenol
(DMSO)

DY-000,039

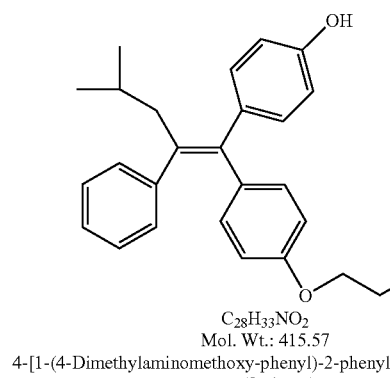

C₂₈H₃₃NO₂
Mol. Wt.: 415.57
Z,E 4-[1-(4-Dimethylaminomethoxy-phenyl)-2-phenyl-4-methylpent-1-
1:1 enyl]-phenol
(DMSO)

DY-000,040

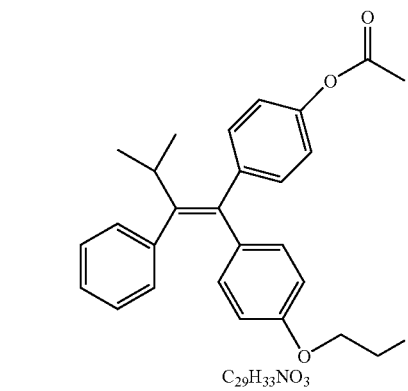

C₂₉H₃₃NO₃
Mol. Wt.: 443.58
(Z,E)- Acetic acid 4-{1-[4-(2-dimethylamino-ethoxy)-phenyl]-3-methyl-2-
1:1 phenyl-but-1-enyl}-phenyl ester
(DMSO)

Novel Compounds 2 do not comprise DY25, DY27, or DY33 because these structures are known in the art.

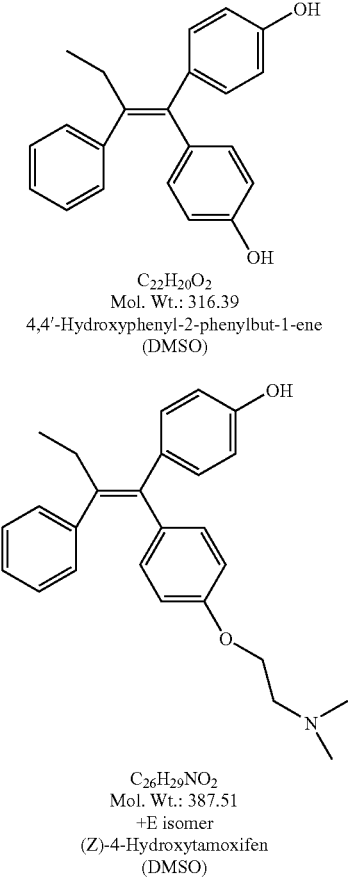

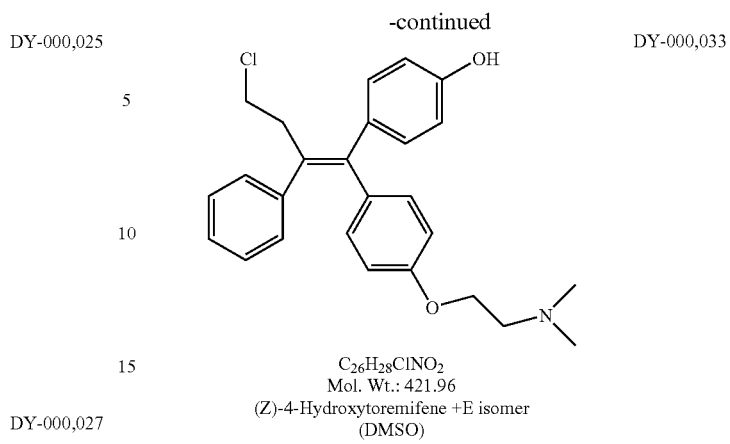

The present invention particularly prefers DY40 as the DY Novel Compound of choice. As the data below shows, all of the Novel DY Compounds from both Novel Compounds 1 and 2 antagonize ERs and ERRs with varying degrees of success. Many of the data show that the Novel Compounds are more efficacious than compounds presently known in the art at modulating ERs, ERRs or modulating both ERs and ERRs. DY40 antagonizes ERα and ERβ with affinities similar to or slightly greater than 4-hydroxytamoxifen. Importantly, DY40 antagonizes ERRβ and ERRγ with a potency about 30-fold greater than 4-hydroxytamoxifen.

MH100×4 is a luciferase reporter with four copies of a GAL4 USAG response element. GAL-L refers to the ligand-binding domain of the indicated receptor fused to the C-terminus of the GAL4 DNA binding domain. Table 1 shows control data comparing the inhibition of ERRs by various doses of tamoxifen.

TABLE 1

| Reporter | Receptor | Reporter Activity | | | | Fold Activation | | | |
| --- | --- | --- | --- | --- | --- | --- | --- | --- | --- |
| | | None | 4-OH Tamoxifen | | | None | 4-OH Tamoxifen | | |
| | | | 1 | 2.5 | 5 | | 1 | 2.5 | 5 |
| MH100x4 | | 0.46 | 0.35 | 0.25 | 0.23 | 1.00 | 0.76 | 0.54 | 0.50 |
| MH100x4 | GAL-ERRa | 6.63 | 7 | 6.5 | 6.13 | 1.00 | 1.06 | 0.98 | 0.92 |
| MH100x4 | GAL-L-ERRb | 1.21 | 0.62 | 0.43 | 0.25 | 1.00 | 0.51 | 0.36 | 0.21 |
| MH100x4 | GAL-ERRg | 0.93 | 0.55 | 0.37 | 0.31 | 1.00 | 0.59 | 0.40 | 0.33 |

Table 2 is control data comparing the inhibition of ERRs by DY14 through DY22.

TABLE 2

| Reporter | Receptor | None | 4-OH Tamoxifen 5 | DY 14 5 | DY 15 5 | DY 16 5 | DY 17 5 | DY 18 5 | DY 19 5 | DY 20 5 | DY 21 5 | DY 22 5 |
| --- | --- | --- | --- | --- | --- | --- | --- | --- | --- | --- | --- | --- |
| Reporter Activity | | | | | | | | | | | | |
| MH100x4 | | 0.49 | 0.12 | 0.48 | 0.4 | 0.35 | 0.39 | 0.26 | 0.37 | 0.35 | 0.31 | 0.28 |
| MH100x4 | GAL-ERRa | 8.54 | 5.09 | 8.63 | 7.06 | 5.63 | 5.18 | 3.39 | 5.27 | 6.39 | 4.34 | 3.35 |
| MH100x4 | GAL-L-ERRb | 1.44 | 0.09 | 1.38 | 1 | 0.71 | 0.76 | 0.6 | 0.84 | 1.01 | 0.65 | 0.64 |
| MH100x4 | GAL-ERRg | 1.25 | 0.16 | 1.38 | 1.11 | 1.14 | 0.91 | 0.73 | 1.02 | 1.01 | 0.71 | 0.63 |

TABLE 2-continued

| Reporter | Receptor | None | 4-OH Tamoxifen 5 | DY 14 5 | DY 15 5 | DY 16 5 | DY 17 5 | DY 18 5 | DY 19 5 | DY 20 5 | DY 21 5 | DY 22 5 |
|---|---|---|---|---|---|---|---|---|---|---|---|---|
| Fold Activation | | | | | | | | | | | | |
| MH100x4 | | 1.00 | 0.24 | 0.98 | 0.82 | 0.71 | 0.80 | 0.53 | 0.76 | 0.71 | 0.63 | 0.57 |
| MH100x4 | GAL-ERRa | 1.00 | 0.60 | 1.01 | 0.83 | 0.66 | 0.61 | 0.40 | 0.62 | 0.75 | 0.51 | 0.39 |
| MH100x4 | GAL-L-ERRb | 1.00 | 0.06 | 0.96 | 0.69 | 0.49 | 0.53 | 0.42 | 0.58 | 0.70 | 0.45 | 0.44 |
| MH100x4 | GAL-ERRg | 1.00 | 0.13 | 1.10 | 0.89 | 0.91 | 0.73 | 0.58 | 0.82 | 0.81 | 0.57 | 0.50 |

Table 3 shows data comparing the inhibition of ERRs by DY25 through DY35.

TABLE 3

| Reporter | Receptor | None | 4-OH Tamoxifen 2.5 | DY 25 2.5 | DY 26 2.5 | DY 27 2.5 | DY 28 2.5 | DY 29 2.5 | DY 30 2.5 | DY 31 2.5 | DY 33 2.5 | DY 34 2.5 | DY 35 2.5 |
|---|---|---|---|---|---|---|---|---|---|---|---|---|---|
| Reporter Activity | | | | | | | | | | | | | |
| MH100x4 | | 0.57 | 0.38 | 0.63 | 0.46 | 0.5 | 0.29 | 0.58 | 0.56 | 0.4 | 0.52 | 0.68 | 0.41 |
| MH100x4 | GAL-ERRa | 8.18 | 8.88 | 9.18 | 9.38 | 8.21 | 8.08 | 8.61 | 8.46 | 8.71 | 9.75 | 8.24 | 6.38 |
| MH100x4 | GAL-L-ERRb | 2.38 | 0.7 | 2.31 | 2.4 | 0.5 | 0.2 | 2.04 | 2.04 | 1.75 | 0.77 | 1.15 | 0.34 |
| MH100x4 | GAL-ERRg | 2.2 | 0.78 | 2.09 | 2.17 | 0.51 | 0.25 | 1.24 | 1.5 | 1.16 | 0.58 | 1.35 | 0.34 |
| Fold Activation | | | | | | | | | | | | | |
| MH100x4 | | 1 | 0.67 | 1.11 | 0.81 | 0.88 | 0.51 | 1.02 | 0.98 | 0.7 | 0.91 | 1.19 | 0.72 |
| MH100x4 | GAL-ERRa | 1 | 1.09 | 1.12 | 1.15 | 1 | 0.99 | 1.05 | 1.03 | 1.06 | 1.19 | 1.01 | 0.78 |
| MH100x4 | GAL-L-ERRb | 1 | 0.29 | 0.97 | 1.01 | 0.21 | 0.08 | 0.86 | 0.86 | 0.74 | 0.32 | 0.48 | 0.14 |
| MH100x4 | GAL-ERRg | 1 | 0.35 | 0.95 | 0.99 | 0.23 | 0.11 | 0.56 | 0.68 | 0.53 | 0.26 | 0.61 | 0.15 |

Table 4 compares inhibition of ERRs by increasing doses of DY39 and DY40.

TABLE 4

| Reporter | Receptor | None | 4-OH Tamoxifen 3 | DY39 0 | DY39 0 | DY39 0.1 | DY39 0.3 | DY39 1 | DY39 3 | None | 4-OH Tamoxifen 3 | DY40 0 | DY40 0 | DY40 0 | DY40 0.1 | DY40 0.3 | DY40 1 |
|---|---|---|---|---|---|---|---|---|---|---|---|---|---|---|---|---|---|
| Reporter Activity | | | | | | | | | | | | | | | | | |
| MH100x4 | | 1.14 | 0.69 | 1.23 | 1.02 | 1.1 | 1.09 | 0.9 | 0.83 | 1.17 | 0.62 | 1.2 | 1.08 | 1.06 | 1.1 | 0.76 | 0.59 |
| MH100x4 | GAL-ERRa | 27.7 | 34.62 | 30.2 | 26.4 | 30 | 30.1 | 33 | 36.2 | 34.05 | 44.33 | 34.34 | 32.4 | 34 | 37 | 40.8 | 27.3 |
| MH100x4 | GAL-L-ERRb | 7.21 | 1.94 | 9.02 | 7.53 | 8.63 | 6.84 | 2.9 | 1.99 | 8.67 | 2.37 | 9.61 | 6.61 | 5.07 | 1.4 | 0.73 | 0.59 |
| MH100x4 | GAL-ERRg | 5.49 | 1.15 | 5.14 | 5.25 | 5.18 | 4.97 | 2.7 | 1.67 | 5.56 | 1.33 | 5.37 | 3.73 | 3.61 | 2 | 1.05 | 0.49 |
| Fold Activation | | | | | | | | | | | | | | | | | |
| MH100x4 | | 1 | 0.61 | 1.08 | 0.89 | 0.96 | 0.96 | 0.8 | 0.73 | 1.03 | 0.54 | 1.05 | 0.95 | 0.93 | 0.9 | 0.67 | 0.52 |
| MH100x4 | GAL-ERRa | 1 | 1.25 | 1.09 | 0.95 | 1.08 | 1.09 | 1.2 | 1.31 | 1.23 | 1.6 | 1.24 | 1.17 | 1.23 | 1.3 | 1.47 | 0.98 |
| MH100x4 | GAL-L-ERRb | 1 | 0.27 | 1.25 | 1.04 | 1.2 | 0.95 | 0.4 | 0.28 | 1.2 | 0.33 | 1.33 | 0.92 | 0.7 | 0.2 | 0.1 | 0.08 |
| MH100x4 | GAL-ERRg | 1 | 0.21 | 0.94 | 0.96 | 0.94 | 0.91 | 0.5 | 0.3 | 1.01 | 0.24 | 0.98 | 0.68 | 0.66 | 0.4 | 0.19 | 0.09 |

Since the DY28, DY35, DY39, and particularly DY40 antagonists inhibit the activity of ERRβ and ERRγ, an aspect of the present invention provides a method for treating any disease that is caused or worsened by the presence of estrogen, estrogen receptors, and/or estrogen related receptors. This embodiment also encompasses any disease that can be treated with an ERR antagonist. Preferably, the disease treated is cancer. More preferably, the disease treated is breast cancer. The disease can be treated by administering a composition of a pharmaceutically effective dose of one or more of the novel preferred DY compounds of choice to the subject in need of treatment. These compounds are estrogen receptor and estrogen related receptor antagonists. The one or more DY compounds antagonize the estrogen-related receptor more effectively than known antagonists currently in clinical use. In a preferred embodiment, the subject is human, the one or more preferred DY compound is DY40, or the ERR antagonist composition comprises DY40.

Another aspect of the present invention provides a method for increasing the efficacy of a variety of treatments for breast cancer by using the antagonizing DY compounds in conjunction with other methods of cancer treatment such as radiotherapeutic agents or chemotherapeutic agents.

Pharmaceutical Indications

Pharmaceutically acceptable carriers for the Novel DY Compositions may include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The formulations useful in the methods of the present invention include one or more ER and/or ERR antagonists, one or more pharmaceutically acceptable carriers therefor, and optionally other therapeutic ingredients. The formulations may conveniently be presented in unit dosage form and may be prepared by any methods well known in the pharmaceutical arts. The amount of active ingredient, which can be combined with a carrier material to produce a single dosage form, will likely vary depending upon the subject being treated and the particular mode of administration. The amount of ER and/or ERR antagonist that can be combined with a carrier material to produce a pharmaceutically effective dose will generally be an amount of the ER and/or ERR antagonist which produces a therapeutic effect. Generally, the amount of the entire volume comprised of the ER and/or ERR antagonist will range from about one percent to about ninety-nine percent of the ER and/or ERR antagonist composition, preferably from about ten percent to about eighty percent of the ER and/or ERR antagonist composition.

Formulations suitable for oral administration may be in the form of capsules, cachets, pills, tablets, lozenges, powders, as granules, bolus, electuary, or a paste, as a solution or a suspension in an aqueous or non-aqueous liquid, as an oil-in-water or water-in-oil liquid emulsion, as an elixir or syrup, or as pastilles (using an inert base, such as gelatin and glycerin, or sucrose and acacia), each containing a predetermined amount of an ER and/or ERR antagonist as an active ingredient.

In solid dosage forms for oral administration, such as capsules, tablets, pills, powders, granules and the like, the ER and/or ERR antagonist is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate, solution retarding agents, such as paraffin, absorption accelerators, such as quaternary ammonium compounds; wetting agents, such as, for example, acetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the ER and/or ERR antagonist therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the ER and/or ERR antagonist(s) only, or preferentially, in a certain portion of the gastrointestinal tract, optionally, in a delayed manner. Examples of embedding compositions that can be used include polymeric substances and waxes. The ER and/or ERR antagonist can also be in microencapsulated form, if appropriate, with one or more of the above-described excipients.

Liquid dosage forms for oral administration include pharmaceutically acceptable emulsions, microemulsions, solutions, suspensions, syrups and elixirs. In addition to the ER and/or ERR modulator(s), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the ER and/or ERR antagonist, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more ER and/or ERR antagonists with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations for the topical or transdermal administration of an ER and/or ERR antagonist or an ER and/or ERR antagonist composition include powders, sprays, ointments, pastes, creams, lotions, gels, solutions, patches and inhalants. The active component may be mixed under sterile conditions with a pharmaceutically acceptable carrier, and with any preservatives, buffers, or propellants that may be required. The ointments, pastes, creams and gels may contain, in addition to the ER and/or ERR antagonist or the ER and/or ERR antagonist composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the ER and/or ERR antagonist or the ER and/or ERR antagonist composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

ER and/or ERR antagonists or ER and/or ERR antagonist compositions can be alternatively administered by aerosol. This is accomplished by preparing an aqueous aerosol, liposomal preparation or solid particles containing the ER and/or ERR antagonists. A nonaqueous (e.g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches can also be used to deliver ER and/or ERR antagonists or ER and/or ERR antagonist compositions to the body. Such formulations can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Formulations suitable for parenteral administration comprise an ER and/or ERR antagonist or an ER and/or ERR antagonist composition in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e.g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, or phenol sorbic acid. It may also be desirable to include isotonic agents, such as sugars, sodium chloride, and the like into the compositions. In addition, prolonged absorption of the injectable pharmaceutical form may be brought about by the inclusion of agents, which delay absorption such as aluminum monostearate and gelatin.

In some cases, in order to prolong the effect of an ER and/or ERR antagonist, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered formulation is accomplished by dissolving or suspending the ER and/or ERR antagonist or ER and/or ERR antagonist composition in an oil vehicle.

Injectable depot forms are made by forming microencapsuled matrices of an ER and/or ERR antagonist or in biodegradable polymers such as polylactide-polyglycolide. Depending on the ratio of the ER and/or ERR antagonist to polymer, and the nature of the particular polymer employed, the rate of drug release can be controlled. Examples of other biodegradable polymers include poly(orthoesters) and poly (anhydrides). Depot injectable formulations are also prepared by entrapping the ER and/or ERR antagonist in liposomes or microemulsions that are compatible with body tissue.

Novel Process for Preparing 1,1-bis (4-hydroxyphenyl)-2-phenylalkenes Derivatives General Overview The novel process via McMurry chemistry can produce many types of 1,1-bis (4-hydroxyphenyl)-2-phenylalkenes. Traditionally, the published methods for the preparation of those 1,1-bis (4-hydroxyphenyl)-2-phenylalkenes were via Friedel-Crafts acylations and Grignard reactions. The precursors for this novel process are generally substituted derivative of 4,4'-dihydroxybenzophenone and are reacted with propiophenone and its derivatives under McMurry reaction conditions. The derivatives have the structure of:

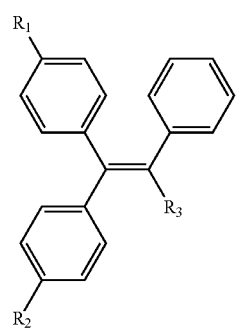

The novel reaction generally proceeds as:

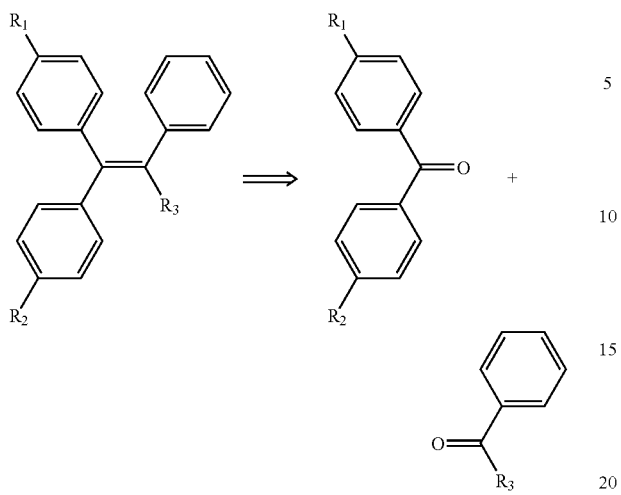

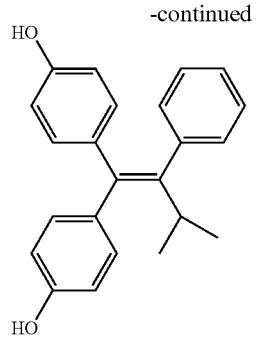

wherein $R_1$, $R_2$, and $R_3$ each optionally represents an alkyl, alkenyl, or alkynyl group, substituents including halogen atoms, haloalkyl and hydroxy groups and optional-substituted alkylcarboxy, alkoxy, alkylamino and alkylcarbonyl groups.

These novel compounds via McMurry reductive coupling do not comprise the structures of 1-[4-(Benzyloxy)phenyl]-1-(4-hydroxyphenyl)-2-phenylbut-1-ene, 1-[4-(Benzyloxy)phenyl]-1-[4-(perfluorotolyloxy)phenyl]-2-phenylbut-1-ene, or (E)-1-(4-Hydroxyphenyl)-1-[4-(trimethylacetoxy)phenyl]-2-phenylbut-1-ene, where R1=OH, $R_2$=OCH$_2$C$_6$H$_5$, or $R_1$=OCH$_2$C$_6$H$_5$, $R_2$=OH; $R_1$=OC$_6$H$_4$CF$_3$, $R_2$=OCH$_2$C$_6$H$_5$, or $R_1$=OCH$_2$C$_6$H$_5$, $R_2$=OC$_6$H$_4$CF$_3$, and $R_1$=OH, $R_2$=OCOC(CH$_3$)$_3$. However, the method of producing these compounds is novel.

A typical process for preparing 1,1-bis(4-hydroxyphenyl)-2-phenylbut-3-methyl-1-ene (1b) involves derivative compound DY40 prepared according to the reaction scheme:

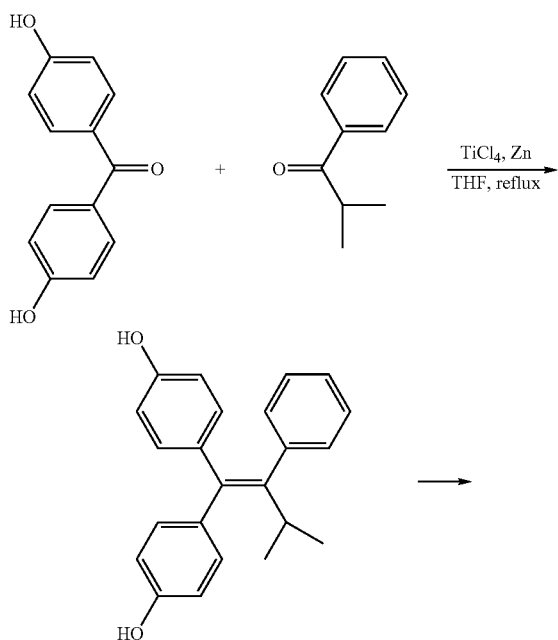

Synthesis of DY40 Overview

Preferably, compounds created by the novel process are two mono-substituted phenyl groups in triarylethylene system. More preferably, the mono-substituted phenyl groups are A and C rings. Most preferably, the novel compound is (E,Z)-4-{1-[4-(2-dimethylamino-ethoxy)-phenyl]-3 methyl-2-phenyl-but-1-enyl}-phenyl acetate (named DY40). DY40 and its derivatives are synthesized using a novel McMurry reductive coupling reaction, with 1,1-bis(4-hydroxyphenyl)-2-phenylalkene analogs as useful building blocks.

Interestingly, the present inventors found that 1,1-bis (4-hydroxyphenyl)-2-phenylbut-1-ene [C2 is substituted by an ethyl (DY-25), isopropyl group (DY-34), 2-chloro-ethyl group (DY-30), 3-chloro-propyl group (DY-31), or propyl group (DY-37)] of the 1,1,2-triarylethene system does not repress ERRs.

The novel compounds are synthesized analogs of 1,1-bis (4-hydroxyphenyl)-2-phenylalkenes as possible templates for a combinatorial or parallel approach in the investigation of dual ER-ERR ligands. Select analogs facilitate the search for potential ligands of ERs and ERRs that are specific for estrogen mediated disorders.

Literature methods for the preparation of 1,1-bis (4-hydroxyphenyl)-2-phenylalkenes are long and proceed in five steps, starting with 1-(4-methoxyphenyl)-2-phenylethan-1-one which was obtained by a Friedel-Crafts acylation of phenylacetyl chloride and anisole. (6,11) The products were reacted with the appropriate alkyl bromides under the influence of potassium tert-butanolate to obtain the C2-alkylsubstituted intermediates. These intermediates were reacted with 4-methoxyphenylmagnesium bromide by the Grignard reaction to yield the corresponding carbinols, which were dehydrated by either phosphoric acid or hydrobromic acid in tetrahydrofuran (THF). The methoxy groups were then converted to hydroxyls substituted on the benzene rings with BBr$_3$ to afford the 1,1-bis (4-hydroxyphenyl)-2-phenylalkenes.

The invention extends to a method of preparing Z- and E-4-hydroxytamoxifen, Z-tamoxifen and its derivatives, especially antiestrogenic derivatives. A "one-pot" synthesis using a McMurry reaction proved to be a simple and efficient pathway to synthesize these useful templates for the 1,1-bis (4-hydroxyphenyl) alkenes. The templates were coupled directly with 2-(dimethylamino)ethyl chloride hydrochloride to afford a series of compounds as a class called DY Novel Compounds 2. Selective crystallization in hexanol gave a 49% yield of (Z)-4-hydroxytamoxifen, and in methanol, a 41% yield of (E)-4-hydroxytamoxifen. This procedure offers an excellent pathway for large-scale industrial production.

A typical process for preparing (Z)-4-hydroxytamoxifen and (E)-4-hydroxytamoxifen is provided below:

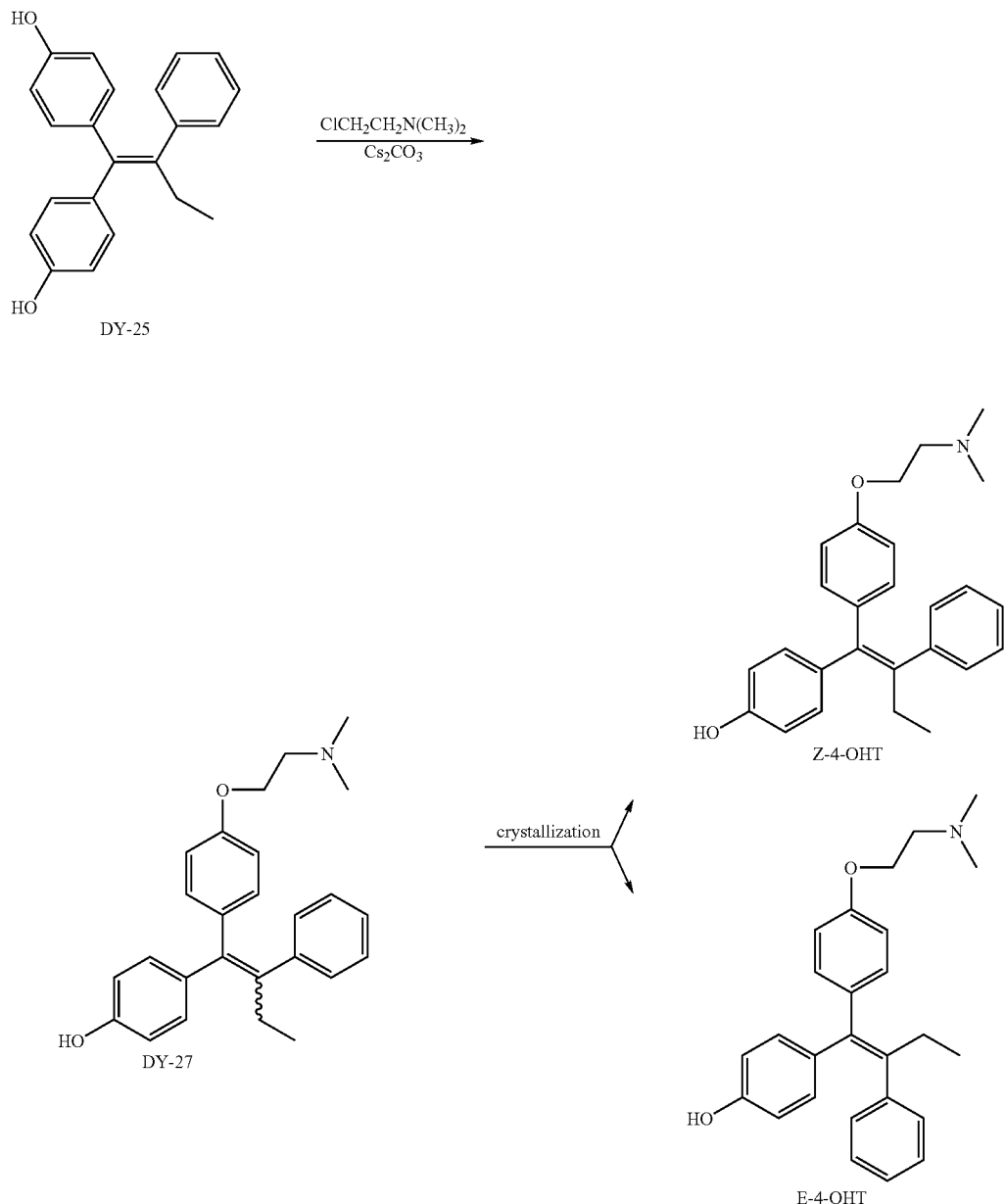

A McMurry reaction is a version of titanium-mediated reductive coupling in which TiCl$_4$-Zn serves as the reductant that completely removes oxygen with the formation of an alkene. (12) Two research groups recently reported utilizing a McMurry reaction as an essential step to furnish analogs of 4-hydroxytamoxifen. (13, 14) The goals of the present experiments were to see if the reaction steps could be reduced and to increase and improve the yields of the desired compounds 1 by using McMurry chemistry with inexpensive starting materials. The McMurry reaction was carried out with a series of commercially available alkyl substituted phenones to couple with 4,4'-dihydroxybenzophenone. The experiment was successful and is outlined as follows:

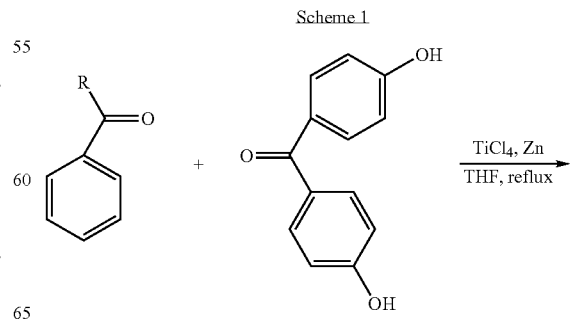

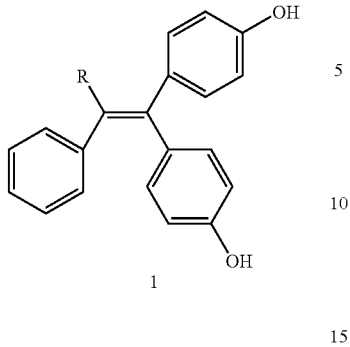

1

Scheme 2

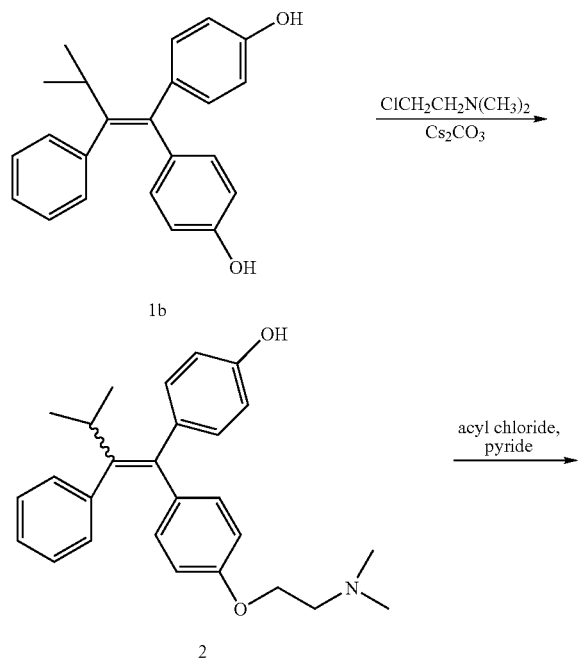

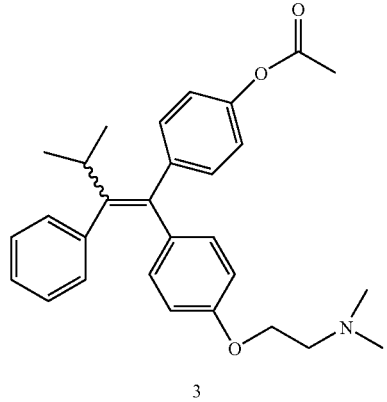

3

2 is a mixture (1:1) of Z (shown)/E isomers.

3 is a mixture (1:1) of E (shown)/Z isomers.

Attention was directed toward further alteration of 1 to produce precursors for derivatives with basic side chains or alkyl substituted on the A or C ring having ER-ERR affinity and an improved antagonistic effect. During a test experiment for preparing parallel synthesis, compound 3 (DY40) (Scheme 2) was identified as an antagonist of ER and ERR, which antagonizes ERα and ERβ with affinities similar to or slightly greater than 4-hydroxytamoxifen. However, Compound 3 antagonizes ERRβ and ERRγ with a potency about 30-fold greater than (Z)-4-hydroxytamoxifen (Scheme 2). Compound 3 (DY 40) consists of geometrical isomers Z and E. The biological activity of Z isomer is uncertain, but since (E)-4 hydroxytamoxifen undergoes a facile isomerization to give a mixture containing the Z isomer, the Z isomer of Compound 3 (DY40) is synthetically useful because it might partially revert to the more active E isomer. (9)

Table 5 data compares inhibition of ERα and ERβ by increasing doses 4-OHT. Table 6 data compares inhibition of ERα and ERβ by increasing doses of compound 3 (DY40).

TABLE 5

| | | | | E2 100 nM | | | | | |
| --- | --- | --- | --- | --- | --- | --- | --- | --- | --- |
| | | None | | 4-OH Tamoxifen [μM] | | | | | |
| Reporter | Receptor | uM: | 0 | 0 | 0.01 | 0.03 | 0.1 | 0.3 |
| Reporter Activity | | | | | | | | | |
| ERE-TK-luc | | 1.16 | 1.13 | 1.2 | 0.98 | 1.58 | 1.48 | 1.61 | 1.34 |
| ERE-TK-luc | ERa | 2.88 | 15.18 | 14.59 | 11.64 | 9.16 | 4.67 | 2.99 | 1.83 |
| ERE-TK-luc | ERb | 2.66 | 12.88 | 10.91 | 8.12 | 5.08 | 3.1 | 2.6 | 1.86 |
| Fold Activation | | | | | | | | | |
| ERE-TK-luc | | 1.00 | 0.97 | 1.03 | 0.84 | 1.36 | 1.28 | 1.39 | 1.16 |
| ERE-TK-luc | ERa | 1.00 | 5.27 | 5.07 | 4.04 | 3.18 | 1.62 | 1.04 | 0.64 |
| ERE-TK-luc | ERb | 1.00 | 4.84 | 4.10 | 3.05 | 1.91 | 1.17 | 0.98 | 0.70 |

TABLE 6

|  |  | None | E2 100 nM | | | | | |
|---|---|---|---|---|---|---|---|---|
|  |  |  |  | DY 40 [µM] | | | | |
|  |  |  | 0 | 0 | 0.01 | 0.03 | 0.1 | 0.3 |
| Reporter Activity |  |  |  |  |  |  |  |  |
| ERE-TK-luc |  | 1.44 | 1.2 | 1.29 | 1.17 | 1.48 | 1.22 | 0.99 | 0.67 |
| ERE-TK-luc | ERa | 3.43 | 16.74 | 13.55 | 8.57 | 5.07 | 2.42 | 1.97 | 1.32 |
| ERE-TK-luc | ERb | 2.88 | 13.11 | 9.37 | 6.03 | 3.19 | 2.36 | 1.58 | 1.09 |
| Fold Activation |  |  |  |  |  |  |  |  |
| ERE-TK-luc |  | 1.00 | 0.83 | 0.90 | 0.81 | 1.03 | 0.85 | 0.69 | 0.47 |
| ERE-TK-luc | ERa | 1.00 | 4.88 | 3.95 | 2.50 | 1.48 | 0.71 | 0.57 | 0.38 |
| ERE-TK-luc | ERb | 1.00 | 4.55 | 3.25 | 2.09 | 1.11 | 0.82 | 0.55 | 0.38 |

Experimental Procedure

For all experiments, commercial organic reagents were purchased from Aldrich Chemical Co. unless otherwise noted and were used without further purification. All solvents were analytical or reagent grade. All reactions were carried out in flame-dried glassware under argon or nitrogen. Melting points were determined and reported automatically by an optoelectronic sensor in open capillary tubes and were uncorrected. $^1$H NMR and $^{13}$C NMR spectra were measured at 500 MHz and 125 MHz respectively, and using CDCl$_3$ or CD$_3$OD as the solvents and tetramethylsilane (Me$_4$Si) as the internal standard. Liquid column chromatography was carried out under moderate pressure by using columns of an appropriate size packed with E. Merck silica gel 60 (230-400 mesh) and eluted with appropriate eluents. All reactions were monitored by TLC on Analtech precoated plates (silica gel HLF).

TLC spots were visualized either by exposure to iodine vapors or by irradiation with UV light. Organic solvents were removed in vacuum using a BUCHI Plas rotary evaporator. All solutions of nonvolatile samples were dried to constant weight on the vacuum pump. Elemental analyses were performed by Desert Analytics, Tucson, Ariz.

Synthesis of DY25

For the creation of the first molecule, DY25 (which is 1,1-Bis (4-hydroxyphenyl)-2-phenylbut-1-ene, using the novel process), the following steps were carried out. To a stirred suspension of zinc powder (2.0 g, 0.031 mole) in dry THF (20 mL), TiCl$_4$ (1.5 mL, 0.014 mol) was added dropwise under Ar, at −10° C. When the addition was complete, the mixture was warmed to room temperature and the refluxed for 2 h. To the cooled suspension of the Titanium reagent was added a solution of 4,4'-hydroxybenzophenone (0.5 g, 0.0023 mol) and propiophenone (1.0 g, 0.0074 mol) in dry THF (40 mL) at 0° C., and the mixture was refluxed in the dark for 2 h. After cooling at room temperature, the reaction mixture was quenched with 10% aqueous potassium carbonate (30 mL) and extracted with EtOAc. The organic layer was washed with brine, dried over MgSO$_4$, and concentrated in vacuo. Flash column chromatography (8:2 hexanes/EtOAc) afforded DY-25 (0.66 g, 91%) as a white solid: mp 200.6° C.; $^1$H NMR (CDCl$_3$) δ 7.16-7.10 (m, 7H), 6.86(d, 2H), 6.74(d, 2H), 6.48 (d, 2H), 4.64(s, 1H), 4.42(s, 1H), 2.49(q, 2H), 0.92(t, 3H): $^{13}$C NMR (CDCl$_3$) δ 157.0, 156.2, 143.8, 141.0, 139.5, 136.0, 135.6, 132.6, 131.2, 130.5, 128.6, 126.0, 115.7, 115.0, 29.5, 13.8. Anal. Calcd for C$_{22}$H$_2$O$_2$: C, 83.51; H, 6.37. Found: C, 83.23; H, 6.58. The structure of DY25 is:

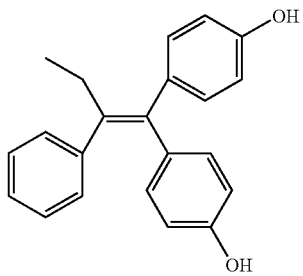

Synthesis of DY34

The next step created DY34, which is 1,1-Bis (4-hydroxyphenyl)-2-phenylbut-3-methyl-1-ene (1b). To a stirred suspension of zinc powder (2.0 g, 0.031 mole) in dry THF (20 mL) was added TiCl$_4$ (1.5 mL, 0.014 mol), under Ar, at −10° C. When the addition was complete, the mixture was warmed to room temperature and the refluxed for 2.5 h. To the cooled suspension of the Titanium reagent was added a solution of 4,4'-hydroxybenzophenone (0.5 g, 0.0023 mol) and isobutyrophenone (1.0 g, 0.0067 mol) in dry THF (40 mL) at 0° C., and the mixture was refluxed in the dark for 3 h. After cooling, the reaction mixture was quenched with 10% aqueous potassium carbonate (30 mL) and extracted with ether. The organic layer was washed with brine, dried over MgSO$_4$, and concentrated in vacuo. Flash column chromatography (8:2 hexanes/EtOAc) afforded 1b (0.68 g, 89%) as a white solid: mp 138.0° C.; $^1$H NMR (CDCl$_3$) δ 7.26-7.17 (m, 5H), 7.11(d, 2H), 7.07(d, 2H), 6.81(d, 2H), 6.44(d, 2H), 4.70(s, 1H), 4.41(s, 1H), 3.04(m, 1H), 0.95(d, 6H): $^{13}$C NMR (CDCl$_3$) δ 157.0, 155.9, 145.9, 141.4, 140.1, 136.1, 135.9, 132.2, 132.1, 131.3, 128.1, 126.7, 115.9, 114.8, 32.8, 22.1. Anal. Calcd for C$_{23}$H$_{22}$O$_2$: C, 83.60; H, 6.71. Found: C, 83.78; H, 6.66. The structure of DY34 is:

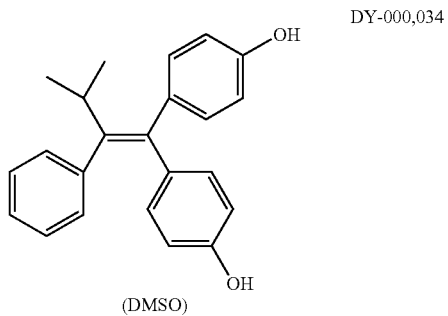

Synthesis of DY35

For the synthesis of DY35, (Z)-4-[1-(4-Dimethylaminomethoxy-phenyl)-3-methyl-2-phenyl-but-1-enyl]-phenol, also called 2, a solution of 1,1-Bis (4 hydroxyphenyl)-2-phenylbut-3-methyl-1-ene (1b) (0.45 g, 0.0014 mol) in DMF (5 mL) was treated with Cs$_2$CO$_3$ (1.06 g, 0.0033 mol) and heated in an oil bath at 80° C. The resulting suspension was treated with 2-(dimethylamino)ethyl chloride hydrochloride (0.75 g, 0.005 mol) in a small potion over a 15 minute period and stirred for 1.5 hours. The reaction mixture was cooled to room temperature, quenched with saturated ammonium chloride (10 mL), and extracted with ethyl acetate (3×10 mL). The combined organic phase was washed with brine (3×10 mL), dried, and concentrated. Flash chromatography (dichloromethanemethanol 9:1) afforded 2 (0.35 g, 64%) as a 1:1 mixture of (E)-2b/(Z)-2a isomers (beige solid): mp: 135.6° C. $^1$H NMR (CD$_3$OD) δ 7.17-7.05 (m, 7H), 6.80(d, 2H), 6.74(d, 2H), 6.38(d, 2H), 4.08(t, 1H), 3.88(t, 1H), 3.02(m, 1H), 2.77 (t, 1H), 2.68(t, 1H), 2.31(s, 3H), 2.29(s, 3H), 0.94(d, 6H). $^{13}$C NMR (CD$_3$OD) δ 157.7, 157.1, 141.3, 139.9, 137.4, 135.7, 132.2, 132.1, 131.3, 128.1, 126.8, 115.9, 114.1, 66.3, 59.0, 45.7, 32.8, 22.1.

Synthesis of DY28

(E,Z)-4-{1-[4-(2-dimethylamino-ethoxy)-phenyl]-2-phenyl-but-1-enyl}-phenyl acetate (DY28) is the acetate of Dimethylaminoethoxy)-phenyl)]-1-(4-hydroxyphenyl)-2-phenyl-but-1-ene (DY27). In the typical process for preparing DY28, 0.5 g (0.0013 mol) of (E,Z)-1-[4-(2- and 0.39 g (0.005 mol) of acyl chloride in pyridine (5 mL) being refluxed for 1 hour. Then, ice water was added, the aqueous layer was extracted with ether, and the organic extracts were washed with saturated NaHCO$_3$ solution. The combined organic phase was washed with brine (3×20 mL), dried, and concentrated. Flash chromatography (dichloromethane-methanol 9:1) afforded colorless oil as a 1:1 mixture of (E)/(Z) isomers, (0.45 g, 82% yield). 1HNMR (CDCl$_3$) δ 7.22 (d, 2H), 7.16 (m, 3H), 7.06 (m, 2H), 6.74 (t, 2H), 6.71(t, 2H), 6.57 (d, 2H), 4.09 (t, 1H), 3.93(t, 1H), 2.76 (t, 1H), 2.62(t, 1H), 2.48 (s, 2H), 2.36 (s, 3H), 2.31 (s, 3H), 2.30 (s, 3H), 0.92(d, 3H). The structure of DY28 is:

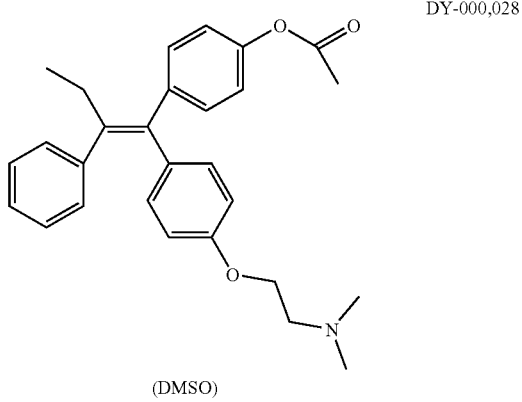

(DMSO)

DY-000,028

Synthesis of DY40

Finally, (E,Z)-4-{1-[4-(2-dimethylamino-ethoxy)-phenyl]-3-methyl-2-phenyl-but-1-enyl}-phenyl acetate (Compound 3) was created and named DY40. For this compound, 0.5 g (0.0012 mol) of (E,Z)-4-[1-(4-Dimethylaminomethoxy-phenyl)-3-methyl-2-phenyl-but-1-enyl]-phenol (Compound 2) and 0.39 g (0.005 mol) of acyl chloride in pyridine (5 mL) were refluxed for an hour. Then, ice water was added, the aqueous layer was extracted with ether, and the organic extracts were washed with saturated NaHCO$_3$ solution. The combined organic phase was washed with brine (3×20 mL), dried, and concentrated.

Flash chromatography (dichloromethane-methanol 9:1) afforded colorless oil as a 1:1 mixture of (E)/(Z) isomers, (0.43 g, 81% yield). 1H NMR (CDCl$_3$) δ 7.78 (d, 2H), 7.16 (m, 3H), 7.07 (m, 4H), 6.92 (d, 2H), 6.88(d, 2H), 6.78(d, 1H), 6.69 (d, 1H), 6.52 (d, 2H), 4.10 (t, 1H), 3.89(t, 1H), 3.04 (m, 1H), 2.75(t, 2H), 2.61 (t, 1H), 2.35 (s, 3H), 2.30 (s, 3H), 2.27 (s, 3H), 0.94(d, 6H). The structure of DY40 is:

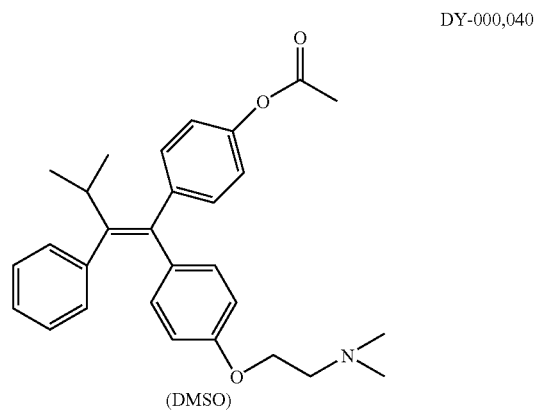

(DMSO)

DY-000,040

The descriptions in the present invention are provided only as examples and should not be understood to be limiting on the claims. Based on the description, a person of ordinary skill in the art may make modifications and changes to the preferred embodiments, which does not depart from the scope of the present invention.

REFERENCES CITED (1) American Cancer Society's Cancer Facts and Figures, www.cancer.org, 2003.
(2) Riggs, L; Hartman, L, Selective Estrogen-Receptor Modulators—Mechanisms of Action and Application to Clinical Practice. New England Journal of Medicine 384:7 2003.
(3) Giguere, V, To ERR in the Estrogen Pathway. Trends in Endocrinology & Metabolism, Review, Vol. 13, No. 5, 2002.
(4) Coward, P.; Lee, D.; Hull, M. V.; and Lehmann, J. M., 4-Hydroxytamoxifen binds to and deactivates the estrogen-related receptor γ, PNAS, 1998, 15, 8880-8884.
(5) Lubczyk, V.; Bachmann, H.; Gust, R., Investigations on estrogen receptor binding. The estrogenic, antiestrogenic, and cytotoxic properties of C2-alkyl-substituted 1,1-bis (4-hydroxyphenyl)-2-phenylethenes, J. Med. Chem. 2002, 45, 5358-5364.
(6) Lubczyk, V.; Bachmann, H.; Gust, R., Antiestrogenically active 1,1,2-tris(4-hydroxyphenyl)alkenes without basic side chain: synthesis and biological activity, J. Med. Chem, 2003.
(7) Finkel T; JBC; 22384348; Schreiber S N; Kralli T; JBC, 278(11), 9013-9018, Mar. 14, 2003.
(8) Katzenellenbogen, B. S.; Norman, M. J.; Eckert, R. L.; Peltz, S. W.; Mangel, W. F., Bioactivities, estrogen-receptor interactions, and plasminogen activator-inducing activities of tamoxifen and hydroxytamoxifen isomers in MCF-7 human-breast cancer-cells Cancer Res. 1984, 44, 112-119.
(9) Schnrider, M. R.; von Angerer, E.; Schonenberger, H.; Michel, R. T.; Fortmeyer, H. P., 1,1,2-Triphenylbut-1-enes: relationship between structure, estradiol receptor affinity, and mammary tumor inhibiting properties J. Med. Chem. 1982, 25, 1070-1077.
(10) Tremblay G B, Bergeron D, Giguere V., Endocrinology; 142(10):4572-5, October 2001.

(11) Dodds, E. C.; Golberg, L.; Lawson, W.; Robinson, R. Synthetic estrogenic compounds related to stilbene and diphenylethane I. *Proc. R. Soc.* London Ser. B 1989, 127, 140-167.

(12) McMurry, J. E.; Fleming, M. P., Improved procedures for the reductive coupling of carbonyls to olefins and for the reduction of diol to olefins, *J. Org. Chem.* 1976, 41, 896.

(13) Gauthier, S.; Mailhot, J.; Labrie, F., New highly stereoselective synthesis of (Z)-4-hydroxytamoxifen and (Z)-4-hydroxytoremifene via McMurry reaction, *J. Org. Chem,* 1996, 61, 3890-3893.

(14) Detsi, A.; Koufaki, M.; Calogeropoulou, T., Synthesis of (Z)-4-hydroxytamoxifen and (Z)-2-[4-[1-(p-hydroxyphenyl)-2-phenyl]-1-butenyl] phenoxyacetic acid, *J. Org. Chem.,* 2002, 67, 4608-4611.

(15) Ichida, M.; Nemoto, S; Finkel, T., Identification of a specific molecular repressor of the peroxisome proliferator-activated receptor gamma Coactivator-1 alpha, *J. Biol Chem,* 2002, 52: 50991-95.

(16) Liu, D.; Zhang, Z.; Gladwell, W.; and Teng, C, Estrogen Stimulates Estrogen-Related Receptor α Gene Expression Through Conserved Hormone Response Elements, Endocrinology, July 2003, 10.1210/en.2003-0432.

(17) Robertson, D. W.; Katzenellenbogen, J. A.; Long, D. J.; Rorke, E. A.; Katzenellenbogen, B. S. *J. Steroid Biochem.* 1982, 16, 1.

(18) Jordan, V. C., Antiestrogens and selective estrogen receptor modulators as multifunctional medicines. 1. Receptor interactions, *J. Med. Chem.,* 2003, 46, 883-908.

(19) Jarman, M.; McCague, R. *J. Chem. Research*(S), 1985, 116.

(20) Magdani, L.; Hutak, A.; Szatmari, E.; Simoni, I.; Halmos, J.; Nemere, F. *Belg. P.,* 1982, 892 662.

OTHER REFERENCES

Karnik, P. S.; Kulkarni, S.; Liu, X. P.; Budd, G. T.; Bukowski, R. M. Estrogen receptor mutations in tamoxifen-resistant breast cancer. Cancer Res. 1994, 54, 349-353.

Giguere, V.; Yang, N.; Segui, P.; Evans, R. M., Identification of a new class of steroid hormone receptors. Nature 1988, 331, 91-94.

Schneider, M. R., 2-Alkyl-substutited 1,1-bis (4-acetoxyphenyl)-2-phenylethenes. Estrogen receptor affinity, estrogenic and antiestrogenic properties, and mammary tumor inhibiting properties. *J. Med. Chem.* 1986, 29, 1494-1498.

What is claimed is:

1. A compound of the structure:

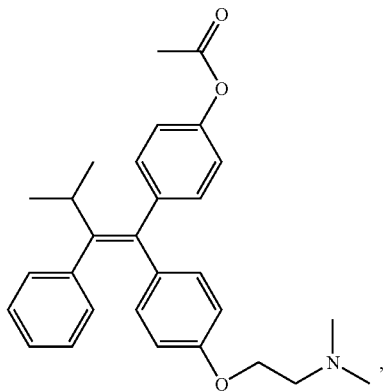

or a salt thereof.

* * * * *